United States Patent [19]

Goegelman

[11] Patent Number: 4,789,684
[45] Date of Patent: Dec. 6, 1988

[54] ANTHELMINTIC FERMENTATION PRODUCTS OF MICROORGANISMS

[75] Inventor: Robert T. Goegelman, Linden, N.J.

[73] Assignee: Merck & Co., Inc., Rahway, N.J.

[21] Appl. No.: 729,520

[22] Filed: May 2, 1985

[51] Int. Cl.$^4$ ............... A61K 31/365; C07D 493/20
[52] U.S. Cl. .................................. 514/450; 549/264
[58] Field of Search ............. 549/264; 514/450, 30, 514/; 534/119

[56] References Cited

U.S. PATENT DOCUMENTS

| | | |
|---|---|---|
| 3,950,360 | 4/1976 | Aoki et al. |
| 4,156,720 | 5/1979 | Fisher et al. ............ 514/30 |
| 4,289,760 | 9/1981 | Mrozik et al. ............ 514/30 |
| 4,310,519 | 1/1982 | Albers-Schonberg et al. |
| 4,378,353 | 3/1983 | Goegelman et al. ............ 435/519 |
| 4,427,663 | 1/1984 | Mrozik ............ 514/30 |
| 4,547,520 | 10/1985 | Ide et al. ............ 549/264 |

*Primary Examiner*—Norma S. Milestone
*Attorney, Agent, or Firm*—David L. Rose; Michael C. Sudol

[57] ABSTRACT

There is disclosed a series of macrolides isolated from the fermentation broth of a microorganism identified as MA-5920. This novel microorganism is formed by the protoplast fusion of strains of *Streptomyces avermitilis* and *Streptomyces hygroscopicus*. The structure of the novel compounds isolated from the microorganism is presented based upon analytical studies. The compounds are highly potent antiparasitic, insecticidal, and anthelmintic agents. Compositions for such uses are also disclosed.

3 Claims, No Drawings

ANTHELMINTIC FERMENTATION PRODUCTS OF MICROORGANISMS

BACKGROUND OF THE INVENTION

The instant novel compounds are related to the avermectin compounds disclosed in U.S. Pat. No. 4,310,519 and the milbemycin compounds disclosed in U.S. Pat. No. 3,950,360. However the instant compounds possess significant structural differences which readily differentiate them from the prior art compounds.

SUMMARY OF THE INVENTION

This invention is concerned with novel chemical compounds. In particular, it is concerned with novel macrocyclic lactones which are produced by the fermentation of a nutrient medium with a strain of the microorganism Streptomyces MA-5920 which was produced by the protoplast fusion of strains of *Streptomyces avermitilis* and *Streptomyces hygroscopicus*. Thus, it is an object of this invention to provide for such novel compounds, and a method for preparing such products microbiologically. It is a further object of this invention to provide for the recovery and purification of such compounds from the fermentation broth. These substances have anti-parasitic and insecticidal activity, in particular anthelmintic, acaracidal and nematocidal activity, and it is, thus, an additional object of this invention to provide novel antiparasitic and insecticidal compositions containing the disclosed compounds. Further objects of this invention will become apparent from the following description of this invention.

DESCRIPTION OF THE INVENTION

In accordance with this invention, novel substances are described, which are prepared by growing under controlled conditions, a previously undescribed strain of microorganism, Streptomyces MA-5920. The compounds are obtained by fermentation and recovered in substantially pure form as described herein.

Based on taxonomic studies, the microorganism capable of producing these compounds is of a new strain of the microorganism Streptomyces. The culture is designated MA-5920 in the culture collection of Merck & Co., Inc., Rahway, N.J. A sample of this culture, capable of producing the herein described compounds, has been deposited, without restriction as to availability, in the permanent culture collection of the American Type Culture Collection at 12301 Parklawn Drive, Rockville, Md. 20852, and has been assigned the accession number ATCC 53110.

The morphological and cultural characteristics of Streptomyces MA-5920 are set forth below:

CULTURAL CHARACTERISTICS OF (V=vegetative growth; A=aerial mycelium; SP=soluble pigment)
Morphology:
  Sporophores form compact spirals, becoming a tight ball. Spores are hygroscopic and as culture ages, the spores coalesce, losing their distinct appearance and becoming an amorphous-like moist area. Electron microscopy showed some spore surfaces as smooth, many as heavily rugose and some as having a short warty appearance.
Oatmeal agar (ISP Medium 3)
  V: Reverse—grayish brown edged with dark gray-brown
  A: Dark gray, good sporulation
  SP: Yellow-brown
Czapek Dox agar (sucrose nitrate agar)
  V: Reverse—cream
  A: Sparse, grayish-white
  SP: None
Glycerol asparagine agar (ISP Medium 5)
  V: Reverse—yellowish brown
  A: medium to dark gray, good sporulation
  SP: Light yellow-brown
Inorganic salts-starch agar (ISP Medium 4)
  V: Reverse—dark gray
  A: Dark gray
  SP: None
Yeast extract-malt extract agar (ISP Medium 2)
  V: Reverse—dark brown
  A: Dark gray, heavy sporulation
  SP: Light yellow-brown
Peptone-iron-yeast extract agar (ISP Medium 6)
  V: Cream to tan
  A: None
  SP: None
  Melanin: Negative
Tyrosine agar (ISP Medium 7)
  V: Dark grayish-brown
  A: None
  SP: Slight browning of medium
  Melanin: Negative
Carbon utilization
  Pridham-Gottlieb basal medium+1% carbon source;
    +=growth; ±=growth poor or questionable;
    −=no growth as compared to negative control (no carbon source)
  Glucose +
  Arabinose +
  Cellulose −
  Fructose +
  Inositol +
  Lactose +
  Maltose +
  Mannitol +
  Mannose +
  Raffinose +
  Rhamnose +
  Sucrose +
  Xylose ±
Temperature range (Yeast extract-dextrose+salts agar)
  28° C.—Good growth and sporulation
  37° C.—Moderate vegetative growth
  42° C.—No growth
  50° C.—No growth
Oxygen requirement (Stab culture in yeast extract-dextrose+salts agar)
  Aerobic All readings taken after three weeks at 28° C. unless noted otherwise. pH of all media approximately neutral (6.8–7.2)

Color number designations taken from Color Harmony Manual, 1958, 4th Edition, Container Corporation of Amercia, Chicago, Ill.

A careful comparison of the foregoing data with published descriptions, including Bergey's Manual of Determinative Bacteriology 9th ed.; Waksman, The Actinomycetes Vol. II (1961); International Journal of Systematic Bacteriology 18, 68–189, 279–392 (1968); 19, 391–512 (1969); 22, 265–394 (1972); shows a correlation between the description of bacterium identified as *Streptomyces hygroscopicus* and the morphological and cultural characteristics of MA-5920. Since the MA-5920 strain meets the standard description of *Streptomyces hygroscopicus*, it is therefore determined that MA-5920 is a strain of the known species *Streptomyces hygroscopicus* and the culture has been given that name. However, there are significant differences between MA-5920 and its two parents. MA-5920 is a much better grower and sporulator than *Streptomyces hygroscopicus*. MA-5920 differs from *Streptomyces avermitilis* in that MA-5920 has a different sporophore configuration and spore surface characteristics and lacks the dark brown soluble pigment. Further, the secondary metabolite products of MA-5920 differ from those produced by the two parent strains. Finally, it is most significantly observed that the products produced by MA-5920 are different from either patent culture. Thus, it is concluded that MA-5920 is a new strain of *Streptomyces hygroscopicus*.

The above description is illustrative of a strain of Streptomyces MA-5920 which can be employed in the production of the instant compounds. However, the present invention also embraces mutants of the above described microorganism. For example, those mutants which are obtained by natural selection or those produced by mutating agents including ionizing radiation such as ultraviolet irradiation, or chemical mutagens such as nitrosoguanidine or the like treatments are also included within the ambit of this invention.

The instant compounds are produced during the aerobic fermentation of suitable aqueous nutrient media under conditions described hereinafter, with a producing strain of Streptomyces MA-5920. Aqueous media such as those used for the production of many antibiotic substances are suitable for use in this process for the production of this macrocyclic compound. Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by Streptomyces MA-5920 in the production of the instant compounds. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalts, manganese, and the like.

It should be noted that the media described hereinbelow and in the Examples are merely illustrative of the wide variety of media, which may be employed, and are not intended to be limitative.

The following are Examples of media suitable for growing strains of Streptomyces MA-5920.

The fermentation employing Streptomyces MA-5920 can be conducted a temperatures ranging from about 20° C. to about 40° C. For optimum results, it is most convenient to conduct these fermentations at a temperature in the range of from about 24° C. to about 30° C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of Streptomyces MA-5920 loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of Streptomyces MA-5920. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 500 RPM and about 2 to 20 cubic feet per minute (CFM) of air.

The novel compounds of this invention are found primarily in the mycelium on termination of the Streptomyces MA-5920 fermentation and may be removed and separated therefrom as described below.

The separation of the novel compounds from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compounds as well as other substances lacking the antiparasitic activity of the instant compounds. If the solvent is a water immiscible one, the layers are separated and the organic solvent is evaporated under reduced pressure. If the solvent is water miscible, it can be extracted with a water immiscible solvent to separate the entrained water. This solvent can then be concentrated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, ethyl acetate, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, dextran gels and the like, as the chromatographic medium, with various solvents and combinations of solvents as the eluent. Thin layer, high pressure, liquid and preparative layer chromatography may be employed to detect the presence of, and to isolate the instant compounds. The use of the foregoing techniques as well as other known to those skilled in the art, will afford purified compositions containing the instant compounds. The presence of the desired compounds is determined by analyzing the various chromatographic fractions for biological activity against selected parasites, or physicochemical characteristics. The structures of the instant compounds has been determined by detailed analysis of the various spectral characteristics of the compounds, in particular their nuclear magnetic resonance, mass, ultraviolet and infrared spectra.

Based on these experimental data, the instant compounds are believed to have the following structural formulae based upon the immediately preceding analytical data:

Compound I assigned as
28-deoxy-6-hydroxy-25-methylmilbemycin B

| HR-MS | Found | Calculated | For | Assignment |
|---|---|---|---|---|
| | 544.3416 | 544.3400 | $C_{32}H_{48}O_7$ | $M^+$ |
| | 153.1281 | 153.1279 | $C_{10}H_{17}O$ | |

Significant fragment ions: 153, 181 define C17-25: 402 loss of 142 (C1-5) from $M^+$ (Note: accompanying loss of C1-6 not observed, as is the general case in B series compounds, thus suggesting modification at C6). Neither 137 (diagnostic C28-deoxy B) nor 151 (diagnostic C28,C6 epoxy A) are observed, again suggesting modification at C6. Since the compound has the same empirical formula as milbemycin $B_1$ but is distinct by MS fragmentation it is presumed to be the alternate C28,C6 epoxy-opened product wherein the hydroxyl group is retained at C6.

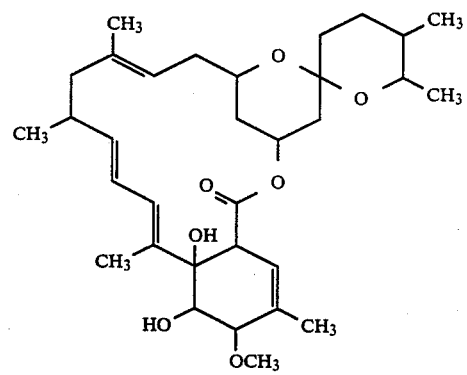

Compound II assigned as
28-deoxy-25-methylmilbemycin B

| HR-MS | Found | Calculated | For | Assignment |
|---|---|---|---|---|
| | 528.3458 | 528.3451 | $C_{32}H_{48}O_6$ | $M^+$ |
| | 510.3344 | 510.3345 | $C_{32}H_{46}O_5$ | $M-H_2O$ |
| | 386.2812 | 386.2821 | $C_{25}H_{38}O_3$ | M-142 |
| | 371.2564 | 371.2586 | $C_{25}H_{35}O_3$ | M-157 |
| | 278.1525 | 278.1518 | $C_{16}H_{22}O_4$ | M-250 |
| | 181.1206 | 181.1229 | $C_{11}H_{17}O_2$ | |
| | 153.1251 | 153.1279 | $C_{10}H_{17}O$ | |
| | 137.0960 | 137.0966 | $C_9H_{13}O$ | |

The compound forms a mono-TMS derivative. Critical fragment ions: 137 (TMS, 209) typical C28-deoxy B series C6-12 fragment; 153, 181 (TMS, unchanged) C17-25; 278 (TMS, 350) M-250, loss of C13-25 from $M^+$; 386, 371 (TMS, 458, unchanged) typical B series loss of C1-5 and C1-6, respectively, from $M^+$.

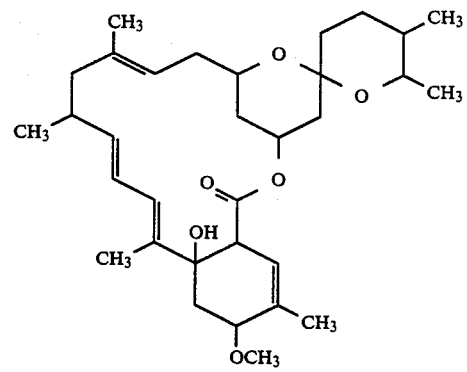

Compound III assigned as
5-demethyl-28-deoxy-25-methyl-5-oxymilbemycin B

| HR-MS | Found | Calculated | For | Assignment |
|---|---|---|---|---|
| | 512.3138 | 512.3138 | $C_{31}H_{44}O_6$ | $M^+$ |
| | 360.1937 | 360.1937 | $C_{21}H_{28}O_5$ | M-152 |
| | 262.1188 | 262.1205 | $C_{15}H_{18}O_4$ | M-250 |
| | 181.1224 | 181.1229 | $C_{11}H_{17}O_2$ | |

The compound forms a di-TMS derivative. Critical fragment ions: 153, 181 (TMS, unchanged) C17-25; 262 (TMS, 406) typical M-250 (C13-25); 360 (TMS, 504) a typical loss of C18-25 from $M^+$.

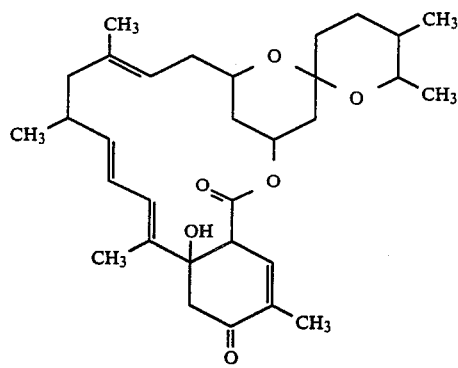

Compound IV assigned as
5-O-demethyl-28-deoxy-25-methylmilbemycin B

| HR-MS | Found | Calculated | For | Assignment |
|---|---|---|---|---|
| | 514.3294 | 514.3294 | $C_{33}H_{46}O_6$ | M+ |
| | 386.2815 | 386.2821 | $C_{25}H_8O_3$ | M-128 |
| | 264.1347 | 264.1362 | $C_{15}H_{20}O_4$ | M-250 |

The compound formed a di-TMS derivative. Critical fragment ions: 137 (TMS, 209) C6-12; 153, 181 (TMS, unchanged) C17-25, 264 (TMS, 408) loss of 250 (C13-25) from M+; 386, 371 (TMS, 458 and unchanged) resulting from loss of C1-5 and C1-6 from M+, respectively, indicating the B series with a hydroxyl at C5.

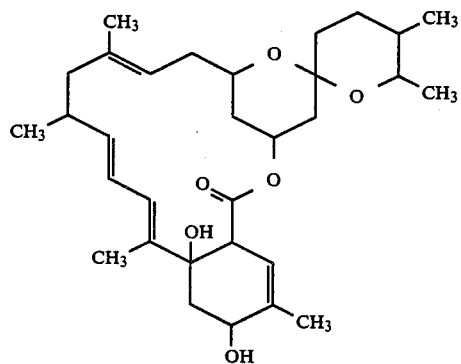

Compound V assigned as
28-deoxy-25-methyl-28-oxomilbemycin B

| HR-MS | Found | Calculated | For | Assignment |
|---|---|---|---|---|
| | 542.3237 | 542.3244 | $C_{32}H_{46}O_7$ | M+ |

The compound forms a mono-TMS derivative. Critical ions: 181, 153 (TMS, unchanged) define the usual C17-25 moiety; 292 (TMS, 364) results from the usual loss of 250 (C13-25) from the molecular ion; 400, 385 (TMS, 472 and unchanged, respectively) indicated the B series with a C5 methoxyl substituent. The compound has an atypical UV maximum at 290 nm supporting the conjugated diene aldehyde structure.

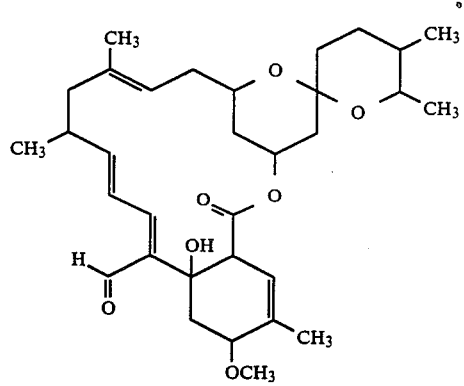

Compound VI assigned as
5-O-demethyl-28-deoxy-25-ethylmilbemycin B

| HR-MS | Found | Calculated | For | Assignment |
|---|---|---|---|---|
| | 528.3444 | 528.3451 | $C_{32}H_{48}O_6$ | M+ |

The compound forms a di-TMS dreivative and contains one less oxygen than milbemycin B1. Critical fragment oins: 137 (TMS, 209), defines C6-12 and is characteristic of B series milbemycins (cf. 151, TMS 223 in milbemycin $B_1$); 167 and 195 (TMS, unchanged), define an additionals $CH_2$ in region C17-25 (up 14 amu from 153, 181 in milbemycin $B_1$); 264 (TMS, 408) loss of 264 (C13-25) from M+; 400 and 385 (TMS, 472 and unchanged) resulting from loss of C1-5 (M-128) and C1-6 (M-143), respectively, indicate that C5 bears a hydroxyl group rather than a methoxyl group as in $B_1$.

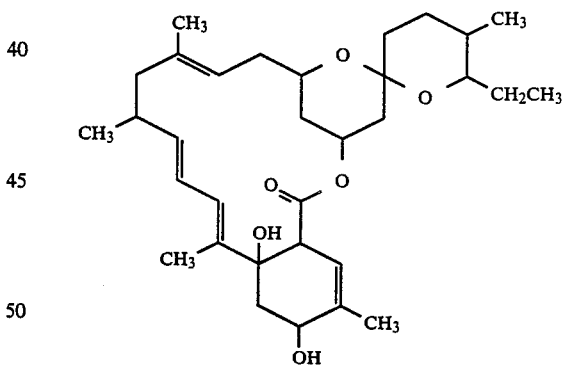

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while other such as Dictyocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica.*

The compounds are also useful against insect pests of stored grains such as Tribolium sp., Tenebrio sp. and of agricultural plants such as spider mites, (Tetranychus sp.), aphids (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agnet. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitable admixed with an acceptable vehicle, preferably of the vegetable oil variety such as peanut oil, cotton seed oil and the like. Other parenteral vehicles such as organic preparations using solketal, glycerol, formal and aqueous parenteral formulations are also sued. The active compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired anti-parasitic result.

In using the compounds of this invention, the individual components may be isolated and purified and used in that form. Alternatively, mixures more of the individual components may be used. It is not necessary to completely separate the various compounds obtained from the purification of the fermentation broth. Generally, there is obtained a mixture containing two or more of the compounds, but having other unrelated compounds excluded therefrom, and such mixture may be used for the prevention and treatment of parasitic diseases as described herein. Such a mixture generally will contain unequal proportions of the compounds, however, all of the compounds have substantial activity and the antiparasitic activity of the mixture can be accurately determined.

In addition, where the instant compounds are to be added to an animal's feed, it is possible to utilize the dried mycelial cake from the fermentation broth. The mycelia contain a preponderance of the activity and since the level of the activity of the mycelia can be determined, it can be added directly to the animal's feed.

The compounds of this invention have a broad spectrum of activity against many internal parasites at low dosage levels and in many different animals. At levels of about 2.5 mg per kg of animal body weight, concentrated mixtures of the instant compounds are fully active in sheep against *Haemonchus contortus, Ostertagia circumcincta, Trichostrongylus axei, Trichostrongylus colubriformis,* Cooperia spp., and *Oesophagostomum columbianum.* Similarly in cattle at dosages as low as 0.043 mg/kg the instant compounds are fully active against *Ostertagia ostertage, Trichostrongylus axei, Trichostrongylus colubriformis, Oesophagostomum radiatum* and *Dictyocaulus viviparus.* In addition, a horse infected with bots (*Gastrophilus intestinalis* and *Gastrophilus haemorrhoidalis*), large and small strongylus and Oxyuris was successfully treated with 10 mg/kg (about 1% active compounds by weight) of a mixed concentrate of the instant compounds, and a dog infected with the microfilarial stage of heartworm (*Dirofilaria immitis*) was successfully treated with a single oral dose at 10 mg/kg (about 1% active compounds by weight) of a mixed concentrate of the instant compounds. In rodents, such as mice, infections of Syphacia, Nematospiroides and Aspiculuris have been successfully treated by the oral administration of the instant compounds or of the concentrates obtained from the extraction of the mycelia.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The anthelmintic activity of the instant compounds may be determined by orally administering via the feed, a sample of the individual compound, a mixture of the compounds, a concentrated extract, and the like to a mouse which had been infected 3 days earlier with *Nematospiroides dubius.* At 11, 12 and 13 days after the initiation of the medication, the faces of the mouse are examined for *N. dubius* eggs, and on the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

EXAMPLE 1

Isolation of the Producing Culture

The producing culture MA-5920 is an isolate obtained from protoplast fusion of *S. avermitilis* MA-4990 and *S. hygroscopicus* MA-4830.

Lyophiles of MA-4990 and MA-4830 were each aseptically transferred to 250 ml baffled Erlenmeyer flasks containing 54 ml of Medium 1 and incubated for 3 days at 28° C. and 220 rpm. Half ml aliquots of the resulting growth were transferred to agar slants of Medium 2. After 10 days incubation at 28°, 5 ml of Medium 3 was aseptically added to a slant of MA-4990, and the surface growth was scraped into the liquid. After 3 minutes of mixing at medium speed in a Fisher Vortex-Genie, 2.5 ml of the suspension was transferred to a 250 ml Erlenmeyer flask containing 50 ml of Medium 3A. Inoculum of MA-4830 was prepared in the same manner, and transferred into 250 ml Erlenmeyer flasks containing 50 ml of either Medium 3 or 3B.

After 2 days of incubation at 28° C. and 220 rpm, the contents of each flask were harvested by centrifugation at 15,000 rpm, 4° C., for 15 minutes, and washed twice with Medium 4. The washed cells from each flask were resuspended in 10 ml of Medium 4 and mixed at medium speed for 3 minutes in the Vortex-Genie.

To a 5 ml aliquot of each, 5 ml of egg white lysozyme suspension (Sigma, 2 mg/ml in Medium 4, sterilized by passage through a 0.2μ filter) was added and mixed by inversion. Each mixture was incubated at ambient temperature for 6 minutes, when conversion to protoplasts was assessed by microscopic examination to be complete.

The suspensions were centrifuged at room temperature in a Beckman TJ-6 clinical centrifuge for 5 minutes at 3000 rpm, and the protoplast pellet washed once in 5 ml of Medium 4. Each washed pellet was resuspended in 5 ml of Medium 4 and one ml aliquots of protoplast suspensions of MA-4990 and MA-4830 were mixed and pelleted again by centrifugation at 3000 rpm for 10 minutes. Each pellet was suspended in 0.2 ml of Medium 4, and 1.8 ml of 40% polyethylene glycol 6000 (Sigma, w/v) in Medium 4 added and mixed by inversion. After 60 seconds at room temperature, the mixture was diluted 5 to 50 fold in Medium 4 and 0.1 ml aliquots spread on agar plates of Medium 5. After 14 days incubation at 28° C., random isolates were transferred to agar plates of Medium 2 and incubated 10 days at 28° C. One of the resulting isolates were designated MA-5920, and was selected for further study because although it resembled MA-4830, this isolate had more abundant sporulation and greater yellow pigment production.

Fermentation for Production of Metabolites

A portion of one colony of MA-5920 was transferred to a baffled 250 ml Erlenmeyer flask containing 54 ml of Medium 1 and shaken at 220 rpm, 28° C., for 3 days. One ml aliquots were then transferred to unbaffled 250 ml Erlenmeyer flasks containing 44 ml of Medium 6 or 7. The flasks were shaken at 220 rpm, 28° C., and at 4 and 8 days ten ml aliquots were taken from each flask and centrifuged in a Beckman TJ-6 clinical centrifuge for 10 minutes at 3000 rpm. To each pellet, 10 ml of $CH_3OH$ was added, the tube mixed, and after 2 hours at room temperature, the extract was cleared by centrifugation for 10 minutes at 3000 rpm. The extracts were analyzed by HPLC.

EXAMPLE 2

A lyophile of MA-5920 was aseptically transferred to a 250 ml baffled Erlenmeyer flask containing 54 ml of Medium 1. The flask was shaken at 220 rpm, 28° C., on a rotary shaker with a 2 inch throw, for 2 days. Two ml of the resulting growth was transferred to an unbaffled 250 ml Erlenmeyer flask containing 44 ml of Medium 8. After 5 days incubation at 28°, 220 rpm, 10 ml aliquots were removed, and the cells pelleted by centrifugation at 3000 rpm, extracted with $CH_3OH$ and analyzed by HPLC.

| Medium 1 | | |
|---|---|---|
| Dextrose | 1.0 | g |
| Dextrin (Fisher) | 10.0 | g |
| Beef Extract (Difco) | 3.0 | g |
| Yeast Autolysate (Ardamine pH, Yeast Prod.) | 5.0 | g |
| NZ Amine Type E (Sheffield) | 5.0 | g |
| $MgSO_4.7H_2O$ | 0.05 | g |
| Phosphate Buffer | 2 | ml |
| $CaCO_3$ | 0.5 | g |
| $dH_2O$ | 1000 | ml |
| pH 7.0–7.2 | | |
| Phosphate Buffer: $KH_2PO_4$ | 91.0 g | |
| $Na_2HPO_4$ | 95.0 g | |
| $dH_2O$ | 1000 ml | |
| pH 7.0 | | |
| Medium 2 | | |
| Yeast Extract (Difco) | 4.0 | g |
| Malt Extract (Difco) | 10.0 | g |
| Dextrose | 4.0 | g |
| $dH_2O$ | 1000 | ml |
| Agar | 20 | g |
| pH 7.2 | | |
| Medium 3 | | |
| Tryptic Soy Broth (Difco) | 30.0 | g |
| $dH_2O$ | 1000 | ml |
| pH 7.3 | | |

-continued

| Medium 3A | | |
|---|---|---|
| Medium 3 supplemented with 0.8% glycine post-sterilization (glycine added as a 20% solution, w/v $dH_2O$, sterilized by passage through a 0.2μ filter) | | |
| Medium 3B | | |
| Medium 3 supplemented with 0.2% glycine post-sterilization (glycine added as a 20% solution, w/v $dH_2O$, sterilized by passage through a 0.2μ filter) | | |
| Medium 4 | | |
| Basal | | |
| Sucrose | 103 | g |
| $K_2SO_4$ | 0.25 | g |
| Trace Element Mix A | 2 | ml |
| $MgCl_2.6H_2O$ | 2.03 | g |
| $dH_2O$ | to 700 | ml |
| Post-sterilization additions, per 700 ml Basal: | | |
| 100 ml of $CaCl_2$ solution (36.8 g/1000 ml $dH_2O$) | | |
| 100 ml of $KH_2PO_4$ solution (0.5 g/1000 ml $dH_2O$) | | |
| 100 ml of Tes solution (0.3 g Tris HCl + 0.1 g EDTA + 0.14 g NaCl in 1000 ml $dH_2O$, adjusted to pH 8.0) | | |
| Medium 5 | | |
| Basal | | |
| Sucrose | 103 | g |
| $K_2SO_4$ | 0.25 | g |
| Glucose | 10 | g |
| L-Asparagine | 1.8 | g |
| Casamino Acids (Difco) | 0.1 | g |
| $MgCl_2.6H_2O$ | 10.12 | g |
| Trace Element Mix A | 2 | ml |
| $dH_2O$ | to 700 | ml |
| Agar | 22.0 | g |
| Post-sterilization additions, per 700 ml Basal: | | |
| 100 ml of $CaCl_2$ solution (29.5 g/1000 ml $dH_2O$) | | |
| 100 ml of $KH_2PO_4$ solution (0.5 g/1000 ml $dH_2O$) | | |
| 100 ml of Tes solution (0.3 g Tris HCl + 0.1 g EDTA + 0.14 g NaCl in 1000 ml $dH_2O$, adjust to pH 8.0) | | |
| Trace Element Mix A Composition: | | |
| $Fe(SO_4)_3.7H_2O$ | 250 | mg |
| $MnCl_2.4H_2O$ | 500 | mg |
| $CuCl_2.2H_2O$ | 25 | mg |
| $CaCl_2.2H_2O$ | 1000 | mg |
| $H_3BO_3$ | 50 | mg |
| $(NH_4)_6Mo_7O_{24}.4H_2O$ | 20 | mg |
| $ZnSO_4.7H_2O$ | 100 | mg |
| $Co(NO_3)_2.6H_2O$ | 20 | mg |
| 0.1N HCl | 1000 | ml |
| Medium 6 | | |
| Dextrin (Fisher) | 40 | g |
| Distillers Solubles (Grain Processing Corp.) | 7 | g |
| Yeast Extract (Oxoid) | 5 | g |
| $CoCl_2.6H_2O$ | 50 | mg |
| $dH_2O$ | 1000 | ml |
| pH 7.3 | | |
| Medium 7 | | |
| Dextrose | 45 | g |
| Peptonized Milk (Sheffield) | 24 | g |
| Ardamine pH (Yeast Products, Inc.) | 2.5 | g |
| Polyglycol 2000 (Dow) | 2.5 | ml |
| $dH_2O$ | 1000 | ml |
| pH 7.0 | | |
| Medium 8 | | |
| Dextrose | 75 | g |
| Peptonized Milk (Sheffield) | 17.5 | g |
| Ardamine pH (Yeast Products, Inc.) | 2.75 | g |
| $dH_2O$ | 1000 | ml |
| pH 7.2 | | |
| Medium 9 | | |
| Dextrose | 2.0% | |
| Yeast Extract (Difco) | 2.0 | |
| Casamino Acids (Difco) | 2.0 | |
| $KNO_3$ | 0.2 | |
| $MgSO_4.7H_2O$ | 0.05 | |
| NaCl | 0.05 | |
| $FeSO_4.7H_2O$ | 0.0025 | |
| $CaCl_2.2H_2O$ | 0.002 | |
| $ZnSO_4.7H_2O$ | 0.001 | |
| $MnSO_4.H_2O$ | 0.0005 | |
| pH 7.0 with NaOH | | |

-continued

| Medium 10 | |
|---|---|
| Dextrose | 0.1% |
| Soluble Starch (Fisher) | 1.0 |
| Beef Extract (Difco) | 0.3 |
| Ardamine pH (Yeast Autolysate) | 0.5 |
| NZ Amine Type E (Sheffield) | 0.5 |
| $MgSO_4.7H_2O$ | 0.005 |
| $KH_2PO_4$ | 0.0182 |
| $Na_2HPO_4$ | 0.0190 |
| $CaCO_3$* | 0.05 |
| pH 7.0–7.2 with NaOH | |
| Medium 11 | |
| Dextrose | 0.1% |
| Soluble Starch (Fisher) | 1.0 |
| Beef Extract (Difco) | 0.3 |
| Yeast Autolysate (Ardamine pH Yeast Products) | 0.5 |
| NZ Amine Type E Sheffield | 0.5 |
| $MgSO_4.7H_2O$ | 0.005 |
| $KH_2PO_4$ | 0.0182 |
| $Na_2HPO_4$ | 0.0190 |
| $CaCO_3$* | 0.05 |
| pH 7.0–7.2 with NaOH | |

*Added after pH adjustment

EXAMPLE 3

Medium Preparation

Medium 9 was prepared with ingredients listed under "Medium Composition: Medium 9". After pH adjustment, 50 ml of the medium was dispensed into each 250 ml, 3-baffled flask. The flasks were plugged with cotton and autoclaved for 20 minutes at 121° C., 16 psi. Following sterilization, the flasks were removed from the autoclave and cooled at room temperature.

Medium 10 was prepared with ingredients previously listed under "Medium Composition: Medium 10". After pH adjustment, 50 ml of the medium was dispensed into each 250 ml unbaffled or three baffled flask. The flasks were plugged with cotton and autoclaved for 20 minutes at 121° C., 16 psi. Following sterilization, the flasks were removed from the autoclave and cooled at room temperature. The flasks were stored at room temperature until use.

Medium 11 was prepared with the ingredients indicated under Medium Composition: "Medium 11". Following pH adjustment and the addition of the calcium carbonate, 50 ml of the well suspended medium was dispersed into each 250 ml, three baffled shake flask. The flasks were plugged with cotton and autoclaved as previously described. Flasks were cooled at room temperature following autoclaving.

Culture Development

1. Culture Storage

MA-4990 was stored in a lyophilized state. Series "c" lyophilized tubes were used for this experiment. MA-5920 was stored as a slant culture on a medium containing (in %): yeast extract 0.4; malt extract 1.0; dextrose 0.4; agar 2.0; pH 7.0. Slants of the culture were prepared by inoculating a slant with vegetative cells, incubating the slants at 28° C. until the slant was well sporulated, and storing the slant under refrigeration until use.

2. MA-4990

A lyophilized tube of this culture was aseptically opened and the contents used to inoculate a flask of Medium 9. The flask was placed on a 220 rpm reciprocating shaker (New Brunswick Scientific, Model G53) with a 2 inch throw in a 28° C. constant temperature room.

After 2 days of incubation in Medium 9, 2 ml of this "seed" culture was transferred to each "production" flask (Medium 10). The production flasks were placed on the 220 rpm shaker in the 28° C. constant temperature room. Two baffled and two unbaffled flasks were harvested at ages of 4, 6 and 8 days and the flasks assayed for milbemycin production using the procedure that follows this section.

23. MA-5920

A section of slant containing this culture was removed and aseptically transferred to a flask of Medium 11. As with the previous culture, the flask was placed on a 220 rpm reciprocating shaker (New Brunswick Scientific, Model G53) in a 28° C. constant temperature room.

After 2 days of incubation in Medium 11, 2 ml of this "seed" culture were transferred to each "production" flask (Medium 10). The production flasks were placed on the 220 rpm shaker in the 28° C. constant temperature room. Two baffled and two unbaffled flasks were harvested at ages of 4, 6, and 8 days and the flasks were assayed for milbemycin production using the procedure that follows this section.

Extraction Procedure

The following procedure was used to prepare the fermentation broth samples for HPLC analysis.

1. The two replicate shake flasks were combined (i.e., 2 days, baffled flask, MA-4990).
2. A 60 ml aliquot of the whole broth was centrifuged for 20 minutes at 9000 rpm, 2° C. in a Sorvall RC-5 centrifuge.
3. The supernatant was decanted, filtered through a $0.45\mu$ millipore filter, and submitted for HPLC analysis.
4. The cell pellet was resuspended in 30 ml acetone and mixed vigorously. This step created a 2×concentrate.
5. The extracted cells were recentrifuged at 3000 rpm in a non-refrigerated Sorvall centrifuge, model GLC-4, for 20 minutes.
6. The acetone fraction was decanted and submitted for HPLC analysis.

EXAMPLE 4

This experiment was the scale-up attempt designed to produce more material. Conditions for this fermentation were extrapolated from the shake flask data from Example 3.

Medium Composition

Same as Example 3; only Media 10 and 11 were used.

Medium Preparation

Medium 10 was prepared in two parts: the cerelose was dissolved in 1.5 liters of distilled water, dispensed into three two liter flasks, plugged with cotton, and autoclaved for 30 minutes at 121° C., 16 psi. The sterile cerelose was aseptically added to the fermentor at inoculation. The peptonized milk and ardamine pH were suspended in 8 liters of distilled water, pH adjusted to 7.0, charged into a 14-liter stirred jar Microferm fermentor (New Brunswick Scientific Model MF-114), and autoclaved for 90 minutes at 121° C., 16 psi.

Medium 11 was prepared as previously indicated. In addition, 300 ml of Medium 11 was distributed into each two liter, three-baffled flask. The two liter flasks were plugged with cotton, the cotton covered with foil, and then were autoclaved for 20 minutes at 121° C., 16 Psi.

Culture Development

A section of slant of MA-5920 was removed from the slant tube and aseptically transferred to a 250 ml, 3-baffled flask of Medium 11. This flask was incubated as previously described in Example 1. After incubating two days, 15 ml from this "seed" culture was transferred to two two liter, 3 baffled "seed" flasks of Medium 11. These flasks were incubated for 24 hours on a 220 rpm reciprocating shaker (New Brunswick Scientific, Model G53) with a 2 inch throw in a 28° C. constant temperature room. Following this incubation, the entire contents of the flasks were aseptically transferred to the 14-liter fermentor containing Medium 10. Prior to inoculation and during the fermentation, the conditions on the fermentor were set to 400 rpm, 0.3 vvm air, 25° C. Polyglycol P-2000 was added as necessary to control foaming but the total amount added did not exceed 0.0001% (v/v).

Samples were removed from the fermentor at twelve hour intervals and were assayed for pH, packed cell volume, ammonia, phosphate, glucose, and milbemycin production.

The fermentation continued for 329 hours at which time it was harvested and sent for isolation.

Analysis for milbemycin production was by HPLC on samples prepared by the method stated in the previous example with the following exceptions: only cell pellets were analyzed, since the first experiment showed most activity in the cell pellet. Also, by altering the volume of acetone added to the cell pellet, the extract could be concentrated as needed.

EXAMPLE 5

The acetone extracts of centrifuged cell pellets from four forty ml fermentations of culture MA-5920 were combined and concentrated to 4 ml with the additional water. The concentrate was then extracted with 3×4 ml of methylene chloride. The extracts were combined and concentrated to dryness. The residue 12.5 mg was taken up in 100 mcl of methylene chloride and chromatographed on an E. Merck Lobar size A silica gel 60 column which had been previously equilibrated with methylene chloride. The chromatography was carried out using a step-wise gradient at 1 ml/min. The gradient consisted of 60 ml each of methylene chloride; 90:10 v/v methylene chloride:ethyl acetate, 85:15 v/v methylene chloride:ethyl acetate, 75:25 v/v methylene chloride:ethyl acetate. After 30 ml of effluent was collected, as a void volume, one hundred and thirty-five one ml fractions were collected. Fractions were combined as follows:

Fractions 53 thru 59 concentrated to dryness and labeled 1.
Fractions 69 thru 78 concentrated to dryness and labeled 2.
Fractions 89 thru 93 concentrated to dryness and labeled 3.
Fractions 104 thru 116 concentrated to dryness and labeled 4.
Fractions 117 thru 135 concentrated to dryness and labeled 5.

EXAMPLE 6

Sample 1 from Example 5 was concentrated to dryness and the residue was taken up in 100 mcl of methanol and chromatographed on a DuPont Zorbax ODS reverse phase C18 column 0.46×25 cm maintained at 60° C. using a solvent system of 85/15 methanol/water at a flow rate of 1 ml/min. The effluent stream was monitored at 240 nm with an LDC Spectromonitor III set at 0.02 AUFS. Four fractions were collected based on the ultra-violet trace. Fraction No. 1 15.2 min. to 16.9 min., fraction No. 2 17.7 min. to 20.0 min., fraction No. 3 23.8 min. to 25.33 min., and fraction No. 4 24.3 min. to 31.0 min. The 4 fractions were concentrated to dryness. Fraction 3 was identified as 28-deoxy-6-hydroxy-25-methylmilbemycin B (Compound I) and Fraction 4 was identified as 28-deoxy-25-methylmilbemycin B (Compound II).

EXAMPLE 7

Seven liters of whole broth from the fermentation of a culture of MA-5920 was filtered using a Super-cel admix and filter precoat. The filtrate, six liters, was discarded. The moist filter cake was slurried with four liters of acetone and stirred overnight. The acetone slurry was filtered and the filter cake discarded. The clear filtrate was concentrated to 500 ml with the addition of water. The aqueous concentrate was then extracted with 3×500 ml of methylene chloride. The extracts were combined, dried with sodium sulfate, and concentrated to 100 ml.

A silica-gel flash chromatography column was dry packed with 325 g of E. Merck silica-gel 60, 0.04 to 0.06 mm particle size, and equilibrated with methylene chloride using 5 psi of air pressure. Fifty ml of the 100 ml of concentrate was applied to the silica-gel and chromatography carried out with a stepwise gradient using 1.3 liters for each step.

Step number 1 methylene chloride
Step number 2 90:10 v/v methylene chloride:ethyl acetate
Step number 3 80:20 v/v methylene chloride:ethyl acetate
Step number 4 70:30 v/v methylene chloride:ethyl acetate
Step number 5 60:40 v/v methylene chloride:ethyl acetate
Step number 6 50:40:10 v/v/v methylene chloride:ethyl acetate-methanol Thirty-two fractions of approximately 250 ml each were collected.

EXAMPLE 8

Fraction 10 from Example 7 was concentrated to an oily residue of 698.1 mg. One ml of methylene chloride was added to the residue, volume 1.7 ml. This solution was chromatographed, in two parts, on a Whatman Partasil silica-gel M9 column 0.94×25 cm maintained at 29° C. using a solvent system of 98:2 v/v methylene chloride:acetonitrile at a flow rate of 10 ml/min. The effluent stream was monitored at 243 nm using an LDC Spectromonitor II with a 1 mm path length cell and a setting of 0.64 AUFS. Fractions were collected on the basis of the ultra-violet trace. Eleven fractions were collected from part one and six fraction part two. Fractions 1 thru 13 from part one and fractions 5 thru 7 from part two were combined.

Fraction No. 11 from example 7 was concentrated to an oily residue of 430.3 mg. One half ml of methylene chloride was added to the residue and the solution chromatographed on a Whatman Partisil silica-gel M9 column, as described above, collecting ten fractions. Fractions 5 thru 7 from this chromatography were combined with the selected fractions from the chromatography of fraction No. 10 and concentrated to dryness. Residue 18.7 mg.

EXAMPLE 9

The 18.7 mg. residue from Example 8 was taken up in 1 ml of methanol and chromatographed on a DuPont Zorbax ODS reverse phase C18 column 2.1×25 cm maintained at 40° C. using a solvent system of 85/15 methanol/water at a flow rate of 10 ml/min. The effluent stream was monitored at 240 nm using an LDC Spectromonitor II with a 1 mm path length cell and a setting of 0.32 AUFS. Ten fractions were collected on the basis of the ultra-violet trace. Fractions 2 thru 4 were combined and concentrated to dryness, affording a residue of 7.7 mg. The residue was taken up in 400 mcl of methanol and rechromatographed on a DuPont Zorbax ODS reverse phase C18 column 0.94×25 cm at room temperature using a solvent system 85/15 methanol/water at 5 ml/min. The effluent stream was monitored at 240 nm using an LDC Spectromonitor II with a 1 mm path length cell and a setting of 0.32 AUFS. Four fractions were collected on the basis of the ultra-violet trace. Fractions 2 and 3 were combined and concentrated to dryness. Residue 4.1 mg which is identified as 5-demethyl-28-deoxy-25-methyl-5-oxomilbemycin B (Compound III).

EXAMPLE 10

Fractions 20 thru 24 from Example 7 were combined and concentrated to dryness, affording a residue of 138.5 mg. The residue was taken up in 1.5 m. of 82:18 v/v methanol:water and chromatographed on a DuPont Zorbax ODS reverse phase C18 column 2.1×25 cm maintained at 40° C. using a solvent system of 82/18 methanol/water at a flow rate of 10 ml/min. the effluent stream was monitored at 240 nm with an LDC Spectromonitor II with a 1 mm path length cell and a setting of 0.32 AUFS. Twenty-two fractions were collected on the basis of the ultra-violet trace. Fractions 21 and 22 were combined and concentrated to a dryness affording a residue of 8.0 mg. which is identified as 5-O-demethyl-28-deoxy-25-methylmilbemycin B (Compound IV).

EXAMPLE 11

Fractions 13 thru 15 from Example 7 were combined and concentrated to dryness affording a residue of 385.7 mg. The residue was taken up in 2 ml of methanol and chromatographed on a DuPont Zorbax ODS reverse phase C18 column 2.1×25 cm maintained at 30° C. using a solvent system of 85/15 methanol/water at a flow rate of 10 ml/min. The effluent stream was monitored at 240 nm with an LDC Spectromonitor II with a 1 mm path length cell and a setting of 0.32 AUFS. Eleven fractions were collected on the basis of the ultra-violet trace. Fraction No. 8 was concentracte to dryness. The compound was found to have an ultra-violet max at 290 nm and was identified as 28-deoxy-25-methyl-28-oxomilbemycin B (Compound V).

EXAMPLE 12

Fractions 16 thru 19 from Example 7 were combined and concentrated to dryness affording a residue of 508.6 mg. The residue was taken up in 2 ml of methanol and chromatographed on a DuPont Zorbax ODS reverse phase C18 column 2.1×25 cm maintained at 30° C. using a solvent system of 85/15 methanol/water at 10 ml/min. The effluent stream was monitored at 240 nm using an LDC Spectromonitor II with a 1 mm path length cell and a setting of 0.32 AUFS. Twenty-three fractions were collected on the basis of the ultra-violet trace. Fractions 21 thru 23 were combined and concentrated to dryness affording 5-O-demethyl-28-deoxy-25-ethylmilbemycin B (Compound VI).

What is claimed is:

1. A compound having the formula:

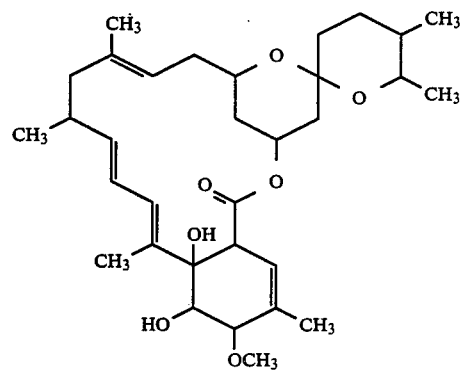

2. A method for the treatment of parasitic diseases in animals which comprises administering to an animal infected with parasites, an effective amount of a compound of claim 1.

3. A composition useful for the treatment of parasitic diseases which comprises an inert carrier and a compound of claim 1.

* * * * *